(12) United States Patent
Salhi et al.

(10) Patent No.: US 9,347,885 B2
(45) Date of Patent: May 24, 2016

(54) METHOD OF DETECTING THALASSEMIA BY OPTICAL ANALYSIS OF BLOOD COMPONENTS

(71) Applicants: Mohamad Saleh Al Salhi, Riyadh (SA); Vadivel Masilamani, Riyadh (SA); Farjah Hassan Algahtani, Riyadh (SA)

(72) Inventors: Mohamad Saleh Al Salhi, Riyadh (SA); Vadivel Masilamani, Riyadh (SA); Farjah Hassan Algahtani, Riyadh (SA)

(73) Assignee: KING SAUD UNIVERSITY, Riyadh (SA)

(*) Notice: Subject to any disclaimer, the term of this patent is extended or adjusted under 35 U.S.C. 154(b) by 594 days.

(21) Appl. No.: 13/889,306

(22) Filed: May 7, 2013

(65) Prior Publication Data

US 2014/0332697 A1 Nov. 13, 2014

(51) Int. Cl.
*G01N 21/64* (2006.01)
*G01N 33/48* (2006.01)
*G01N 33/49* (2006.01)
*G01N 33/68* (2006.01)

(52) U.S. Cl.
CPC .......... *G01N 21/6486* (2013.01); *G01N 33/492* (2013.01); *G01N 33/6812* (2013.01)

(58) Field of Classification Search
CPC ... G01N 21/64; G01N 21/6486; G01N 33/48; G01N 33/49; G01N 33/492; G01N 33/68; G01N 33/6812; Y10T 436/145555; Y10T 436/147777; Y10T 436/173845
USPC ............. 436/63, 66, 86, 89, 96, 98, 106, 111, 436/164, 172; 422/82.05, 82.08; 435/29; 250/459.1
See application file for complete search history.

(56) References Cited

U.S. PATENT DOCUMENTS

| 5,589,932 | A | 12/1996 | Garcia-Rubio et al. |
| 6,322,981 | B1 | 11/2001 | Rodgers et al. |
| 2002/0122168 | A1 | 9/2002 | Garcia-Rubio et al. |
| 2003/0137649 | A1 | 7/2003 | Riordan et al. |
| 2009/0046286 | A1 | 2/2009 | Masilamani et al. |
| 2010/0075367 | A1 | 3/2010 | Masilamani et al. |
| 2012/0016818 | A1 | 1/2012 | Hackett et al. |
| 2012/0052516 | A1 | 3/2012 | Baudin-Creuza et al. |

OTHER PUBLICATIONS

Masilamani et al. Photodiagnosis and Photodynamic Therapy, vol. 10, Jun. 13, 2013, pp. 429-433.*
Daniel E. Duggan et al., "The Spectrophotofluorometric Determination of Tryptophan in Plasma and of Tryptophan and Tyrosine in Protein Hydrolysates," Journal of Biological Chemistry, 1956, 223, 313-319.
L. V. Hankes et al., "Tryptophan Metabolism in Humans with Various types of Anemias," Blood, 1968, 32(4), 649-661.
Digambara Patra et al., "Recent Developments in Multi-Component Synchronous Fluorescence Scan Analysis," Trends in Analytical Chemistry, 2002, 21(12), 787-798.
Kan-Zhi Liu et al., "Infrared Spectroscopic Identification of β-Thalassemia," Clinical Chemistry, 2003, 49(7), 1125-1132.
M. S. Al Salhi, A. A. Al Hazmi, V. Masilamami, A. S. Al Dwayyau, O. A. Al Daghri, H. S. Al Salhi, F. M. Al Othman, Al Azhar, Bull, "Spectral Characterization of Sickle Cell anaemia patients". Al-Azhar Bull. Sci., 17 (2006) 13-24.
Ming Han et al., "The Alterations of Tyrosine and Tryptophane Residues Along with the Evolution of Tumor: Determination by Synchronous Fluorescence Spectra," Scientific Research and Essays, Jan. 2012, 7(2), 165-169.
Qian Liu et al., "A Novel Rapid Method for Simultaneous Determination of Three Diagnostically Important Porphyrins in Erythrocytes Using Hyphenated Synchronous Fluorescence Techniques," Talanta, 2012, 88, 663-668.

* cited by examiner

*Primary Examiner* — Maureen Wallenhorst
(74) *Attorney, Agent, or Firm* — Richard C. Litman

(57) ABSTRACT

The method of detecting thalassemia by optical analysis of blood components is a spectral detection method that is based on the fluorescence spectra of a set of biomolecules, including tyrosine, tryptophan, nicotinamide adenine dinucleotide, and flavin adenine dinucleotide, which are all found in blood plasma, and porphyrin, which is found in red blood cells (RBCs). Measured ratios of intensity maxima between tryptophan and nicotinamide adenine dinucleotide, flavin adenine dinucleotide and nicotinamide adenine dinucleotide, tyrosine and tryptophan, and the normal form of porphyrin and the basic form of porphyrin may each be used, alone or in combination, to diagnose a patient as suffering from thalassemia.

12 Claims, 3 Drawing Sheets

METHOD OF DETECTING THALASSEMIA BY OPTICAL ANALYSIS OF BLOOD COMPONENTS

BACKGROUND OF THE INVENTION

1. Field of the Invention

The present invention relates generally to spectroscopic methods for the analysis of blood components, and particularly to a method of detecting thalassemia by optical analysis of blood components that uses fluorescent spectroscopy to determine measured ratios of intensity maxima between tryptophan and nicotinamide adenine dinucleotide (NADH), flavin adenine dinucleotide (FAD) and nicotinamide adenine dinucleotide, tyrosine and tryptophan, and the normal form of porphyrin and the basic form of porphyrin.

2. Description of the Related Art

Thalassemia is a form of inherited autosomal recessive blood disorder. In thalassemia, the disease is caused by the weakening and destruction of red blood cells. Thalassemia is caused by variant or missing genes that affect how the body makes hemoglobin, Hemoglobin is the protein in red blood cells that carries oxygen. People with thalassemia make less hemoglobin and fewer circulating red blood cells than normal, which results in mild or severe anemia. Thalassemia can cause significant complications, including pneumonia, iron overload, bone deformities and cardiovascular illness.

Normally, hemoglobin is composed of four protein chains, two α and two β globin chains arranged into a heterotetramer. In thalassemia, patients have defects in either the α or β globin chain (unlike sickle-cell disease, which produces a specific mutant form of β globin), causing production of abnormal red blood cells. The thalassemias are classified according to which chain of the hemoglobin molecule is affected. In α thalassemias, production of the α globin chain is affected, while in β thalassemia production of the β globin chain is affected.

The β globin chains are encoded by a single gene on chromosome 11; α globin chains are encoded by two closely linked genes on chromosome 16. Thus, in a normal person with two copies of each chromosome, there are two loci encoding the β chain, and four loci encoding the α chain. Deletion of one of the α loci has a high prevalence in people of African or Asian descent, making them more likely to develop a thalassemias. β Thalassemias are not only common in Africans, but also in Greeks and Italians.

The most common method of detection of thalassemia involves performance of a complete blood count (CBC), followed by electrophoreses and molecular diagnosis, such as high-performance liquid chromatography (HPLC) and genotyping using the polymerase chain reaction (PCR). This process, however, requires the usage of highly specialized equipment, thus making detection both expensive and difficult.

Thus, a method of detecting thalassemia by optical analysis of blood components solving the aforementioned problems is desired.

SUMMARY OF THE INVENTION

The method of detecting thalassemia by optical analysis of blood components is a spectral detection method that is based on the fluorescence spectra of a set of biomolecules, including tyrosine, tryptophan, nicotinamide adenine dinucleotide, and flavin adenine dinucleotide, which are all found in blood plasma, and porphyrin, which is found in red blood cells (RBCs).

In a first embodiment, synchronous fluorescence excitation spectroscopy is performed on a blood plasma sample from a patient. The fluorescence intensity maxima in an excitation band corresponding to tryptophan and nicotinamide adenine dinucleotide are identified and measured. Then, an intensity ratio is defined as a ratio of measured fluorescence intensity of tryptophan to measured fluorescence intensity of nicotinamide adenine dinucleotide. The patient may then be diagnosed as suffering from thalassemia if the intensity ratio is above 5.5.

In addition to the above intensity ratio, or as a replacement therefor, the fluorescence intensity maximum in the excitation band corresponding to flavin adenine dinucleotide is also identified and measured. A secondary intensity ratio is defined as a ratio of measured fluorescence intensity of flavin adenine dinucleotide to the measured fluorescence intensity of nicotinamide adenine dinucleotide. The patient may then be additionally diagnosed as suffering from thalassemia if the secondary intensity ratio is above 1.3.

As a further addition to the above intensity ratios, or as a replacement therefor, the fluorescence intensity maximum in the excitation band corresponding to tyrosine is also identified and measured. A third intensity ratio is defined as a ratio of measured fluorescence intensity of tyrosine to the measured fluorescence intensity of tryptophan. The patient may then be additionally diagnosed as suffering from thalassemia if the tertiary intensity ratio is between about 0.9 and about 2.1.

In addition to spectral analysis of the blood plasma sample, fluorescence emission spectroscopy may be performed on a red blood cell sample from the patient. The fluorescence intensity maxima in an emission band corresponding to a basic form of porphyrin and a normal form of porphyrin are identified and measured. An intensity ratio related to porphyrin is then defined as a ratio of measured fluorescence intensity of the normal form of porphyrin to measured fluorescence intensity of the basic form of porphyrin. A porphyrin intensity ratio in the range of between about 0.5 and about 1.0 indicates that the patient suffers from thalassemia.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
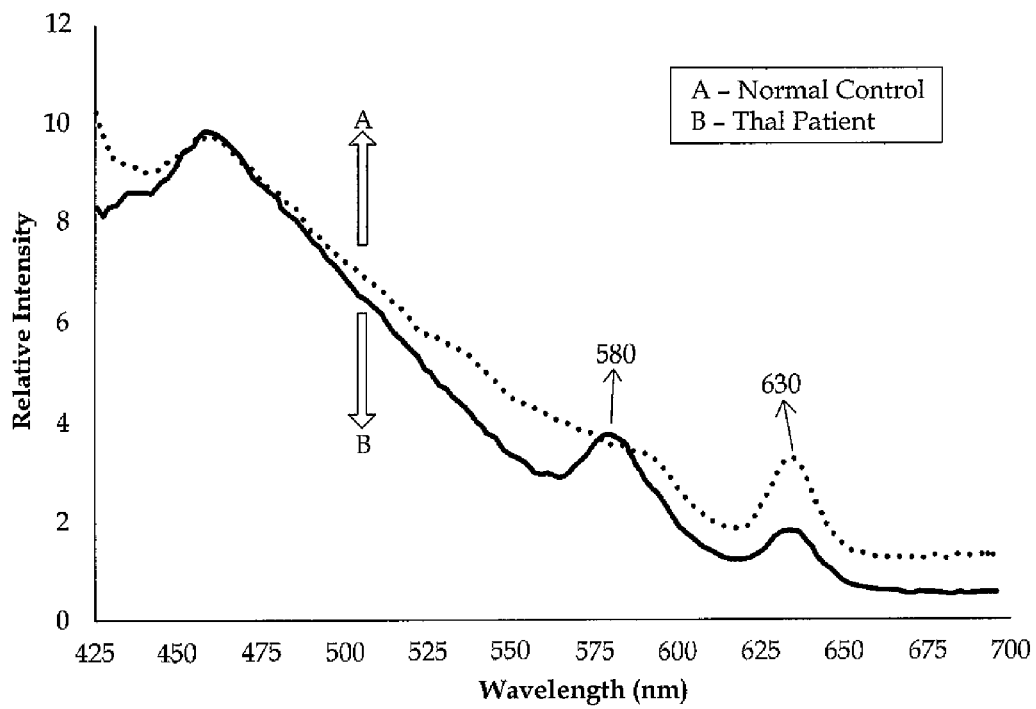
FIG. 1 is a graph illustrating relative intensities as a function of emission wavelength of acetone extracts of red blood samples taken from a control group and from patients suffering from Thalassemia using fluorescence emission spectroscopy.

The method of detecting thalassemia by optical analysis of blood components is a spectral detection method that is based on the fluorescence spectra of a set of biomolecules, including tyrosine, tryptophan, nicotinamide adenine dinucleotide, and flavin adenine dinucleotide, which are all found in blood plasma, and porphyrin, which is found in red blood cells (RBCs).

In experiments, the present method was tested with blood samples taken from 18 healthy human volunteers (i.e., the control group) and 21 patients who had already tested positive for thalassemia. For the control group, a blood sample of exactly 5 mL of venous blood was extracted from each volunteer, with the volunteers having ages ranging from 17 to 32. Each sample was collected in a violet, sterile vial. Each vial contained an ethylenediaminetetraacetic acid (EDTA) anticoagulant. Each vial was then gently rocked five times for adequate mixing of the EDTA and the whole blood. The vial was then centrifuged at 3,000 RPM for fifteen minutes, producing a clear, pale, greenish-yellow plasma as a supernatant. 1.5 mL of the plasma was pipetted out from the top layer for spectrofluorometric analysis, leaving the buffy coat of the formed element sediment undisturbed. The blood plasma samples were subjected to synchronous fluorescence excitation spectral analyses in this form, without any other treatment of the plasma.

The buffy coat was then pipetted out of the vial and discarded. Exactly one mL of thick formed elements from the bottom layer of the vial were then pipetted and drawn into a sterile vial containing 2 mL of analytical grade acetone. After a thorough mixing, the vial was centrifuged at 3,000 RPM for fifteen minutes. The resultant supernatant was subjected only to fluorescence emission spectra with a wavelength of excitation at 400 nm.

For the patients already diagnosed with thalassemia, the same process was carried out. Patient samples from patients with both α and β major thalassemia were obtained from King Khalid University Hospital in Riyadh, Saudi Arabia. The 21 patients had ages ranging between 17 and 32, with the median age being 25 years of age.

Upon initial inspection, the ratio between the volume of plasma and the cellular component for the control samples was about 1.2 to 1, but the ratio for the thalassemia samples as found to be almost 1.8 to 1. The plasma of the control samples had a greenish-yellow color, and the plasma in the thalassemia samples had a yellowish color.

Spectral readings were taken by a spectrofluorometer. In experiment, an LS 55 fluorescence spectrometer manufactured by PERKINELMER® Incorporated of Massachusetts, although it should be understood that any suitable type of spectrofluorometer may be utilized. The LS 55 fluorescence spectrometer is capable of taking excitation, emission and synchronous spectra in the range of 200-800 nm. An excitation and emission slit width of 10 nm was used, along with a scan speed of 1,000 nm/min. Mono-wavelength light with a spectral width of 10 nm and a spot size of 3×2 mm was allowed to fall on the sample, which was contained in a quartz cuvette. The power at the point of illumination was about 20 μW, which is low enough such that there is no photo-bleaching effect. Analysis was performed in triplicate for each sample. Synchronous fluorescence excitation spectra (SXS) were obtained with an offset of 70 nm between the excitation and emission gratings.

It is well known that the red blood cell (RBC) content is significantly lower in thalassemia patients. In the samples collected, the RBC count for the thalassemia patients varied between 2 million/μL and 3.5 million/μL, with a mean of 3 million/μL. In contrast, the RBC values for the normal control samples varied between 4.5 million/μL and 5.75 million/μL, with a mean of 5 million/μL. This is shown in the spectral analysis of FIG. 1, which illustrates the fluorescence spectra of the acetone extract of cellular components. In FIG. 1, the curve labeled "A" illustrates the relative spectral intensities for the control samples, and the curve labeled "B" illustrates the relative spectral intensities for the thalassemia patients (labeled as "Thal" in FIGS. 1-6).

The fluorescence emission spectroscopy (FES) of the acetone extract of cellular components of blood in FIG. 1 shows excitation of both control and thalassemia samples excited at 400 nm. Both samples have peaks at 470 nm, mostly due to the Raman band of acetone in which the fluorescence biomolecules are floating. Two more peak bands can be seen at 580 nm and 630 nm, the first being from the basic form of porphyrin and the second one being from the normal form of porphyrin. Defining an intensity ratio $R_1$ as $R_1=I_{630}/I_{580}$, then an $R_1$ value of about 1.2 indicates a normal, healthy sample, and an $R_1$ value of about 0.5 indicates a sample with thalassemia.

Figure 2:
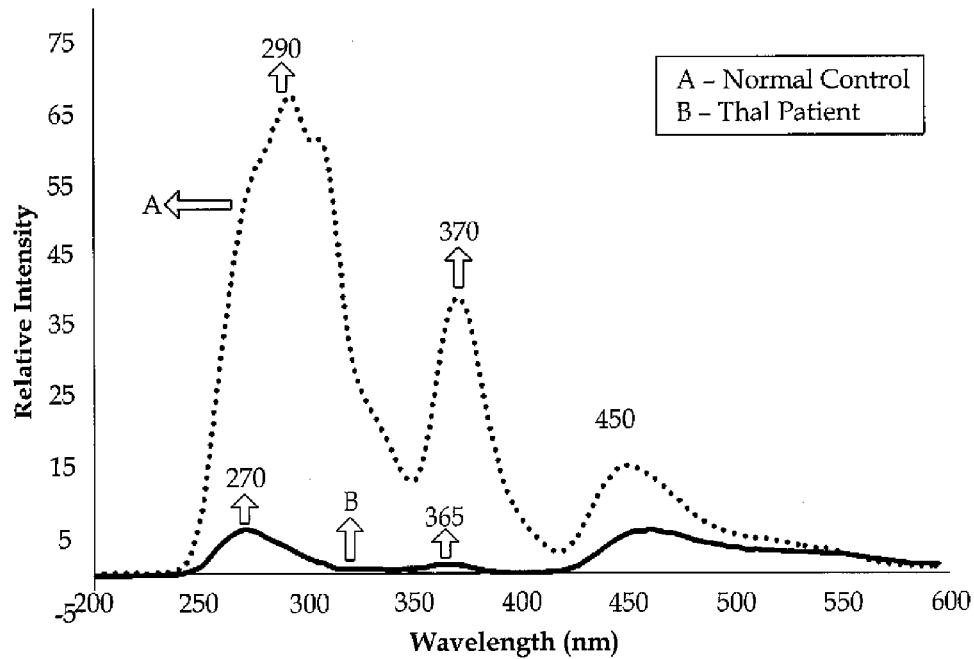
FIG. 2 is a graph illustrating relative intensities as a function of excitation wavelength of blood plasma samples taken from a control group and from patients suffering from thalassemia using synchronous fluorescence excitation spectroscopy.

FIG. 2 shows the synchronous fluorescence excitation spectra (SXS) for both the control samples (the "A" curve) and for samples of the thalassemia patients (the "B" curve). In the control group, peaks can be seen at 290 nm, 370 nm and 450 nm. The peak at 290 nm corresponds to the excitation peak of the amino acid tryptophan, the peak at 370 nm corresponds to that of the coenzyme nicotinamide adenine dinucleotide (NADH), and the peak at 450 nm corresponds to that of the metabolite flavin adenine dinucleotide (FAD). It should be noted that there is a shoulder at 275 nm due to the amino acid tyrosine, which occurs on the shorter wavelength side of the first peak (at 290 nm). The relative intensity of these peaks are 65 for the 290 nm band, 40 for the 370 nm band, 15 for the 450 nm band, and about 50 for the 275 nm shoulder.

In contrast, the "B" curve in FIG. 2 for the thalassemia samples shows that the peaks in the thalassemia samples are out of proportion, and the overall intensities of the thalassemia samples are significantly low. Defining the relative intensity ratio $R_2=I_{290}/I_{370}$ (the ratio of intensities of the peak due to tryptophan and that due to NADH), then $R_2$ has a value of 1.6 for the healthy, control samples, but $R_2$ has a value of 6.2 for the thalassemia samples. In other words, the two fluorescent biomarkers tryptophan and NADH are out of proportion for the thalassemia patients. The ratio $R_2$ is about four times greater in thalassemia patients than it is in the control group.

Figure 3:
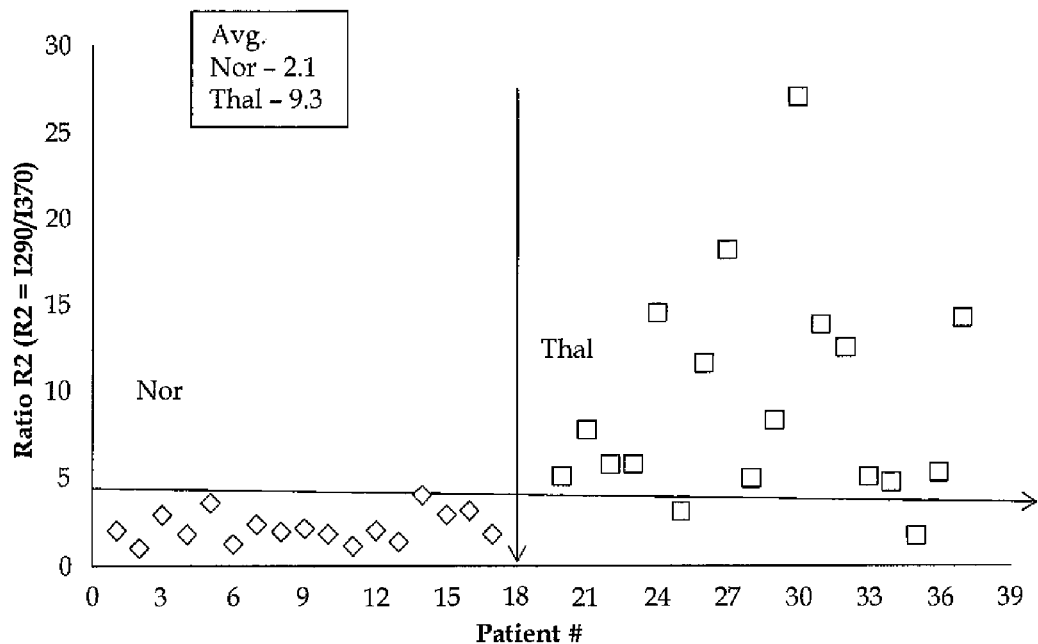
FIG. 3 is a plot showing an intensity ratio of measured fluorescence intensity of tryptophan to measured fluorescence intensity of nicotinamide adenine dinucleotide for the control group and the patients suffering from thalassemia using the synchronous fluorescence excitation spectroscopy of FIG. 2.

In order to show the level of the discrimination between the two sets, FIG. 3 shows the two sets classified almost into two distinct categories, with a mean of 2.1 for the control and 9.3 for the patients. This change in the relative intensities may arise due to an increase of intensity at the 290 nm peaks or due to the decrease at 370 nm.

Figure 4:
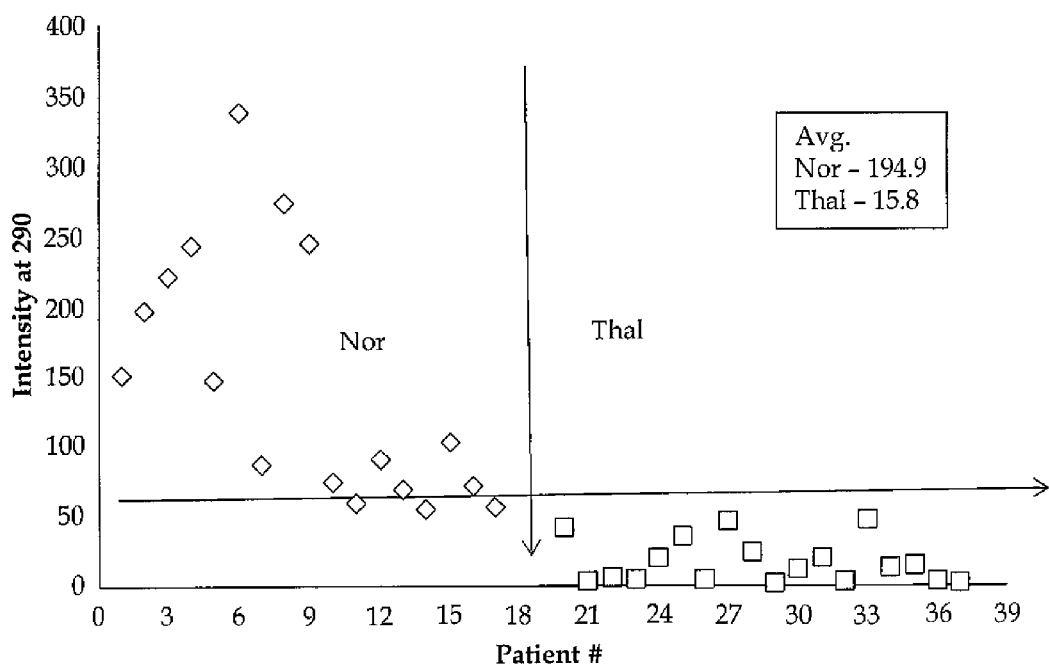
FIG. 4 is a plot showing intensities at an excitation wavelength of 290 nm for the control group samples and the samples from the patients suffering from thalassemia using the synchronous fluorescence excitation spectroscopy of FIG. 2.

FIG. 4 shows the distribution of intensities at 290 nm for the control and thalassemia samples. It can be seen that the peak at 290 nm is about twelve times lower for the thalassemia patients than for the control group. Although not shown in this graph, it has been found that at 370 nm, the intensity is far less for the thalassemia patients than for the control group. This indicates that in the plasma of the thalassemia patients, concentration of tryptophan and NADH are both lower than for the control samples, but the decrease is more pronounced for NADH than for tryptophan.

Figure 5:
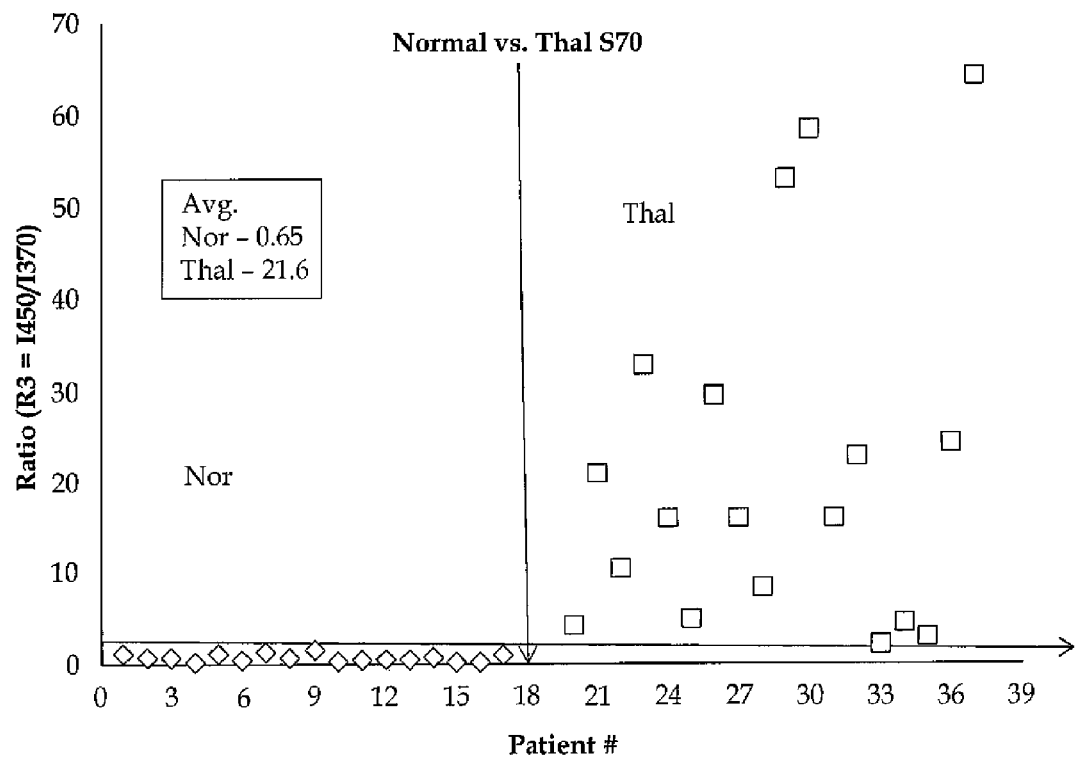
FIG. 5 is a plot showing a secondary intensity ratio of measured fluorescence intensity of flavin adenine dinucleotide to the measured fluorescence intensity of nicotinamide adenine dinucleotide for the control group and the patients suffering from thalassemia using the synchronous fluorescence excitation spectroscopy of FIG. 2.

In a similar manner, the classification was performed based on an intensity ratio $R_3 = I_{450}/I_{370}$, where the peak at 450 nm is due to FAD and that at 370 nm is due to NADH, as illustrated in FIG. 5. It can be seen that the mean value of $R_3$ is 0.65 for the control group and 21.6 for the thalassemia patients. From this window of classification, specificity and sensitivity above 96% may be achieved. This is because the level of FAD is abnormally high for the thalassemia patients.

Figure 6:
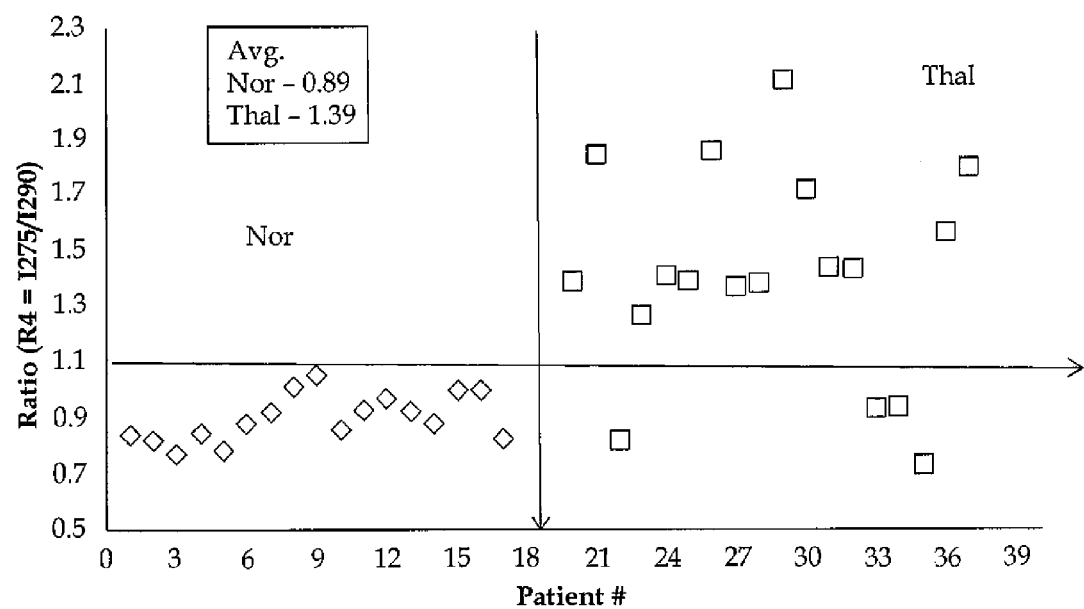
FIG. 6 is a plot showing a third intensity ratio of measured fluorescence intensity of tyrosine to the measured fluorescence intensity of tryptophan for the control group and the patients suffering from thalassemia using the synchronous fluorescence excitation spectroscopy of FIG. 2.

It should be noted that there is a relative elevation of the peak at 275 nm, in comparison to that of 290 nm for the thalassemia patients, as shown in FIG. 6. The control samples have a clear distinct band at 290 nm in the ultraviolet (UV) region, with a weak shoulder at 275 nm, however this is seen to be the opposite in the thalassemia patients. Defining a fourth ratio $R_4 = I_{275}/I_{290}$, R4 is found to be about 0.8 in the control group, but rises from 0.9 to 2.1, with an average of 1.4, in the thalassemia patients; i.e., the peak at 275 nm due to tyrosine is elevated by 75% over that of the control samples.

It is to be understood that the present invention is not limited to the embodiments described above, but encompasses any and all embodiments within the scope of the following claims.

We claim:

1. A method of detecting thalassemia by optical analysis of blood components, comprising the steps of:
   performing synchronous fluorescence excitation spectroscopy on a blood plasma sample from a patient;
   identifying and measuring fluorescence intensity maxima in an excitation band corresponding to tryptophan and nicotinamide adenine dinucleotide;
   defining an intensity ratio as a ratio of measured fluorescence intensity of tryptophan to measured fluorescence intensity of nicotinamide adenine dinucleotide; and
   diagnosing the patient as suffering from thalassemia if the intensity ratio is about 6.2.

2. The method of detecting thalassemia by optical analysis of blood components as recited in claim 1, further comprising the steps of:
   identifying and measuring a fluorescence intensity maximum in the excitation band corresponding to flavin adenine dinucleotide;
   defining a second intensity ratio as a ratio of measured fluorescence intensity of flavin adenine dinucleotide to the measured fluorescence intensity of nicotinamide adenine dinucleotide; and
   diagnosing the patient as suffering from thalassemia if the second intensity ratio is about 21.6.

3. The method of detecting thalassemia by optical analysis of blood components as recited in claim 2, further comprising the steps of:
   identifying and measuring a fluorescence intensity maximum in the excitation band corresponding to tyrosine;
   defining a third intensity ratio as a ratio of measured fluorescence intensity of tyrosine to the measured fluorescence intensity of tryptophan; and
   diagnosing the patient as suffering from thalassemia if the third intensity ratio is between about 0.9 and about 2.1.

4. The method of detecting thalassemia by optical analysis of blood components as recited in claim 3, further comprising the steps of:
   performing fluorescence emission spectroscopy on a red blood cell sample from the patient;
   identifying and measuring fluorescence intensity maxima in an excitation band corresponding to a basic form of porphyrin and a normal form of porphyrin;
   defining a porphyrin intensity ratio as a ratio of measured fluorescence intensity of the normal form of porphyrin to measured fluorescence intensity of the basic form of porphyrin; and
   diagnosing the patient as suffering from thalassemia if the porphyrin intensity ratio is in the range of about 0.5 to about 1.0.

5. A method of detecting thalassemia by optical analysis of blood components, comprising the steps of:
   performing synchronous fluorescence excitation spectroscopy on a blood plasma sample from a patient;
   identifying and measuring fluorescence intensity maxima in an excitation band corresponding to flavin adenine dinucleotide and nicotinamide adenine dinucleotide;
   defining an intensity ratio as a ratio of measured fluorescence intensity of flavin adenine dinucleotide to measured fluorescence intensity of nicotinamide adenine dinucleotide; and
   diagnosing the patient as suffering from thalassemia if the intensity ratio is greater than 1.3.

6. The method of detecting thalassemia by optical analysis of blood components as recited in claim 5, further comprising the steps of
   identifying and measuring a fluorescence intensity maximum in the emission band corresponding to tryptophan;
   defining a second intensity ratio as a ratio of measured fluorescence intensity of tryptophan to the measured fluorescence intensity of nicotinamide adenine dinucleotide; and
   diagnosing the patient as suffering from thalassemia if the second intensity ratio is greater than 5.0.

7. The method of detecting thalassemia by optical analysis of blood components as recited in claim 6, further comprising the steps of:
   identifying and measuring a fluorescence intensity maximum in the excitation band corresponding to tyrosine;
   defining a tertiary intensity ratio as a ratio of measured fluorescence intensity of tyrosine to the measured fluorescence intensity of tryptophan; and
   diagnosing the patient as suffering from thalassemia if the tertiary intensity ratio is between about 0.9 and about 2.1.

8. The method of detecting thalassemia by optical analysis of blood components as recited in claim 7, further comprising the steps of:
   performing fluorescence emission spectroscopy on a red blood cell sample from the patient;
   identifying and measuring fluorescence intensity maxima in an excitation band corresponding to a basic form of porphyrin and a normal form of porphyrin;
   defining a porphyrin intensity ratio as a ratio of measured fluorescence intensity of the normal form of porphyrin to measured fluorescence intensity of the basic form of porphyrin; and diagnosing the patient as suffering from thalassemia if the porphyrin intensity ratio is in the ration between about 0.5 to about 1.0.

9. A method of detecting thalassemia by optical analysis of blood components, comprising the steps of:
performing synchronous fluorescence excitation spectroscopy on a blood plasma sample from a patient;
identifying and measuring fluorescence intensity maxima in an excitation band corresponding to tryptophan and tyrosine;
defining an intensity ratio as a ratio of measured fluorescence intensity of tyrosine to measured fluorescence intensity of tryptophan; and
diagnosing the patient as suffering from thalassemia if the intensity ratio is between about 0.9 and about 2.1.

10. The method of detecting thalassemia by optical analysis of blood components as recited in claim 9, further comprising the steps of:
identifying and measuring a fluorescence intensity maximum in the excitation band corresponding to nicotinamide adenine dinucleotide;
defining a second intensity ratio as a ratio of measured fluorescence intensity of tryptophan to the measured fluorescence intensity of nicotinamide adenine dinucleotide; and
additionally diagnosing the patient as suffering from thalassemia if the second intensity ratio is greater than 5.0.

11. The method of detecting thalassemia by optical analysis of blood components as recited in claim 10, further comprising the steps of:
identifying and measuring a fluorescence intensity maximum in the excitation band corresponding to flavin adenine dinucleotide;
defining a third intensity ratio as a ratio of measured fluorescence intensity of flavin adenine dinucleotide to the measured fluorescence intensity of nicotinamide adenine dinucleotide; and
diagnosing the patient as suffering from thalassemia if the third intensity ratio is greater than 1.3.

12. The method of detecting thalassemia by optical analysis of blood components as recited in claim 11, further comprising the steps of:
performing fluorescence emission spectroscopy on a red blood cell sample from the patient;
identifying and measuring fluorescence intensity maxima in an emission band corresponding to a basic form of porphyrin and a normal form of porphyrin;
defining a porphyrin intensity ratio as a ratio of measured fluorescence intensity of the normal form of porphyrin to measured fluorescence intensity of the basic form of porphyrin; and
diagnosing the patient as suffering from thalassemia if the porphyrin intensity ratio is in the range between about 0.5 to about 1.0.

* * * * *